(12) United States Patent
Lim et al.

(10) Patent No.: US 9,308,646 B2
(45) Date of Patent: Apr. 12, 2016

(54) APPARATUS AND METHOD FOR CONTROLLING FORCE TO BE USED FOR MOTION OF SURGICAL ROBOT

(71) Applicant: Samsung Electronics Co., Ltd., Suwon-si (KR)

(72) Inventors: Soo Chul Lim, Seoul (KR); Joon Ah Park, Hwaseong-si (KR); Hyung Joo Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 334 days.

(21) Appl. No.: 13/731,344

(22) Filed: Dec. 31, 2012

(65) Prior Publication Data

US 2013/0289767 A1    Oct. 31, 2013

(30) Foreign Application Priority Data

Apr. 30, 2012  (KR) .................. 10-2012-0045523

(51) Int. Cl.
 B25J 9/00 (2006.01)
 B25J 9/16 (2006.01)
 A61B 19/00 (2006.01)

(52) U.S. Cl.
 CPC ........... *B25J 9/1633* (2013.01); *A61B 19/2203* (2013.01); *A61B 2019/2223* (2013.01); *A61B 2019/2292* (2013.01); *A61B 2019/2296* (2013.01); *G05B 2219/39505* (2013.01); *G05B 2219/39523* (2013.01); *G05B 2219/40138* (2013.01); *G05B 2219/40619* (2013.01); *G05B 2219/45117* (2013.01)

(58) Field of Classification Search
 CPC .............. B25J 9/1633; A61B 19/2203; A61B 2019/2223; A61B 2019/2292; A61B 2019/2296; G05B 2219/39505; G05B 2219/39523; G05B 2219/40138; G05B 2219/40619; G05B 2219/45117
 See application file for complete search history.

(56) References Cited

U.S. PATENT DOCUMENTS

| | | | | |
|---|---|---|---|---|
| 5,214,969 A | * | 6/1993 | Adkins | A24C 5/32 131/908 |
| 5,649,956 A | * | 7/1997 | Jensen | B25J 9/1065 403/316 |
| 6,574,355 B2 | * | 6/2003 | Green | H04N 13/0497 348/E13.014 |
| 7,313,464 B1 | * | 12/2007 | Perreault | B25J 9/1666 318/568.1 |
| 8,350,806 B2 | * | 1/2013 | Nagasaka | G06F 3/016 345/156 |
| 9,050,719 B2 | * | 6/2015 | Valpola | B25J 9/1694 |
| 2004/0140787 A1 | * | 7/2004 | Okamoto | B25J 13/083 318/568.21 |
| 2004/0186624 A1 | * | 9/2004 | Oda | B25J 9/1697 700/245 |
| 2004/0243147 A1 | * | 12/2004 | Lipow | A61B 19/22 606/130 |
| 2005/0273086 A1 | * | 12/2005 | Green | A61B 19/2203 606/1 |

(Continued)

FOREIGN PATENT DOCUMENTS

| | | |
|---|---|---|
| JP | 2002-159509 | 6/2002 |
| JP | 2003-019683 | 1/2003 |

(Continued)

*Primary Examiner* — Jonathan L Sample
(74) *Attorney, Agent, or Firm* — NSIP Law

(57) ABSTRACT

An apparatus and method for controlling a robot may scale a motion of a surgical robot based on a type of object gripped by the surgical robot. In the robot controlling method, by scaling the motion of the surgical robot based on the type of object gripped by the surgical robot, the surgical robot may automatically perform the motion on objects using an optimized force although a user does not control a force minutely based on the type of object gripped by the surgical robot.

26 Claims, 11 Drawing Sheets

(56) References Cited

U.S. PATENT DOCUMENTS

| | | | |
|---|---|---|---|
| 2006/0116973 A1* | 6/2006 | Okamoto | B25J 5/007 706/16 |
| 2007/0219668 A1* | 9/2007 | Takahashi | B25J 15/0009 700/249 |
| 2007/0265638 A1* | 11/2007 | Lipow | A61B 19/22 606/130 |
| 2008/0059131 A1* | 3/2008 | Tokita | G06F 3/011 703/5 |
| 2008/0204425 A1* | 8/2008 | Nagasaka | G06F 3/016 345/173 |
| 2009/0018700 A1* | 1/2009 | Okamoto | B25J 13/083 700/260 |
| 2010/0217528 A1* | 8/2010 | Sato | B25J 9/1666 701/301 |
| 2010/0291520 A1* | 11/2010 | Kurenov | A61B 17/0469 434/262 |
| 2011/0190932 A1* | 8/2011 | Tsusaka | B25J 13/08 700/254 |
| 2012/0191245 A1* | 7/2012 | Fudaba | B25J 9/1633 700/254 |
| 2014/0195052 A1* | 7/2014 | Tsusaka | A61B 19/2203 700/257 |

FOREIGN PATENT DOCUMENTS

| | | |
|---|---|---|
| JP | 2009-045428 | 3/2009 |
| KR | 10-2006-0114195 | 11/2006 |
| KR | 10-2008-0047318 | 5/2008 |
| KR | 10-2008-0100212 | 11/2008 |
| KR | 10-2010-0077615 | 7/2010 |
| KR | 10-2011-0005829 | 1/2011 |
| KR | 10-2011-0010836 | 2/2011 |
| KR | 10-2011-0075025 | 7/2011 |
| KR | 10-2011-0081153 | 7/2011 |
| WO | 2009/123891 A1 | 10/2009 |
| WO | 2010/039394 A1 | 4/2010 |
| WO | 2010/048160 A3 | 4/2010 |

* cited by examiner

FIG. 2B

[Table 1]

DB

| Object n | Stiffness | Fracture force | ... | Yield Strength |
|---|---|---|---|---|
| Object 1 | Stiffness | Fracture force | ... | Yield Strength |
| Stretch | oo1 N/m | xx1 N | | xo1 MPa |
| Compression | oo2 N/m | xx2 N | | xo2 MPa |

FIG. 2C

[Table 2]

DB1: Suture

| Suture type 1 | Stiffness | Fracture force | ... | Yield Strength |
|---|---|---|---|---|
| Stretch | oo1 N/m | xx1 N | | xo1 MPa |
| Compression | oo2 N/m | xx2 N | | xo2 MPa |

FIG. 2D

[Table 3]

DB2: Organ

| Organ n | Stiffness | Fracture force | ... | Yield Strength |
|---|---|---|---|---|

| Organ 1 | Stiffness | Fracture force | ... | Yield Strength |
|---|---|---|---|---|
| Stretch | oo1 N/m | xx1 N | | xo1 MPa |
| Compression | oo2 N/m | xx2 N | | xo2 MPa |

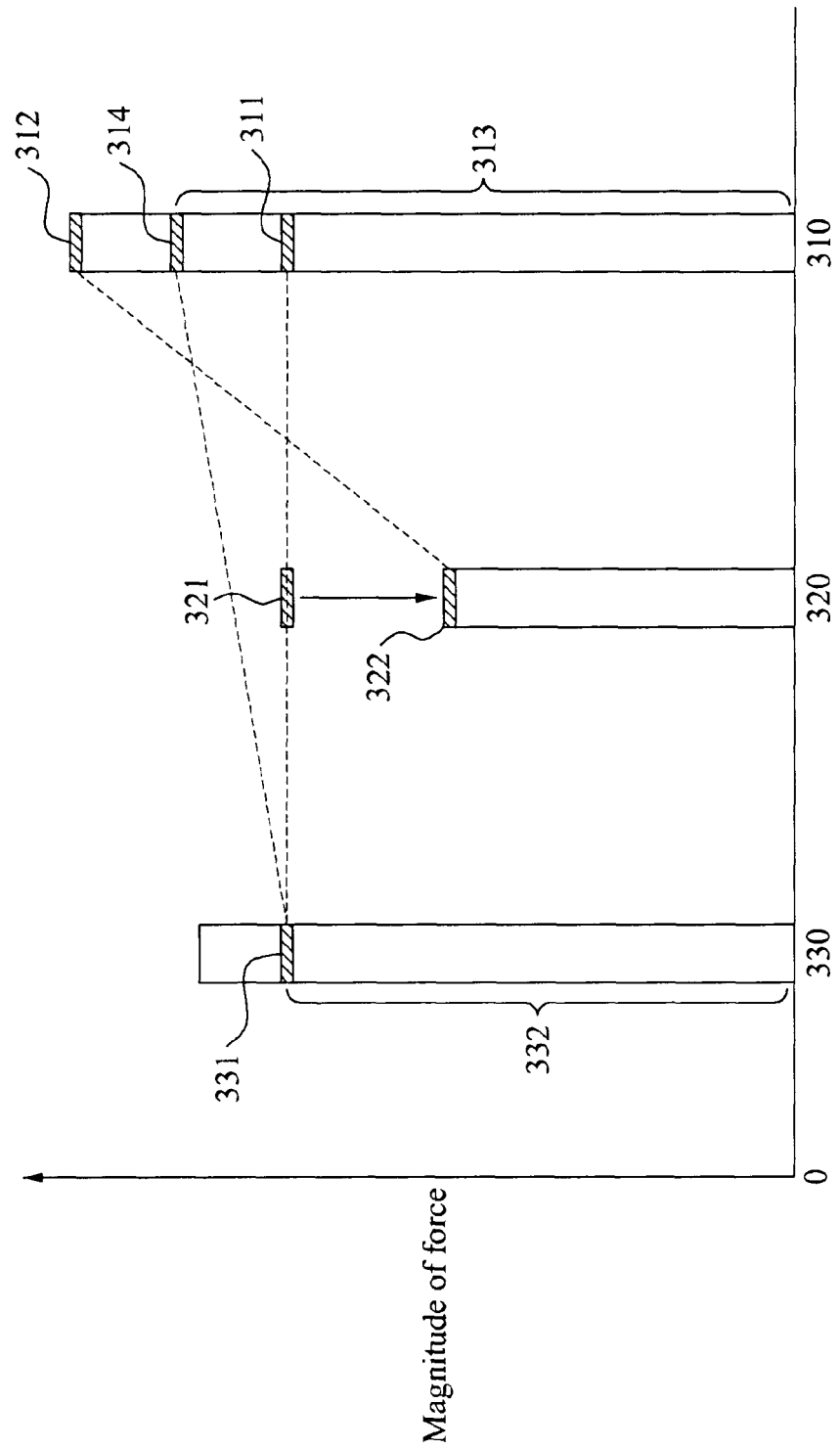

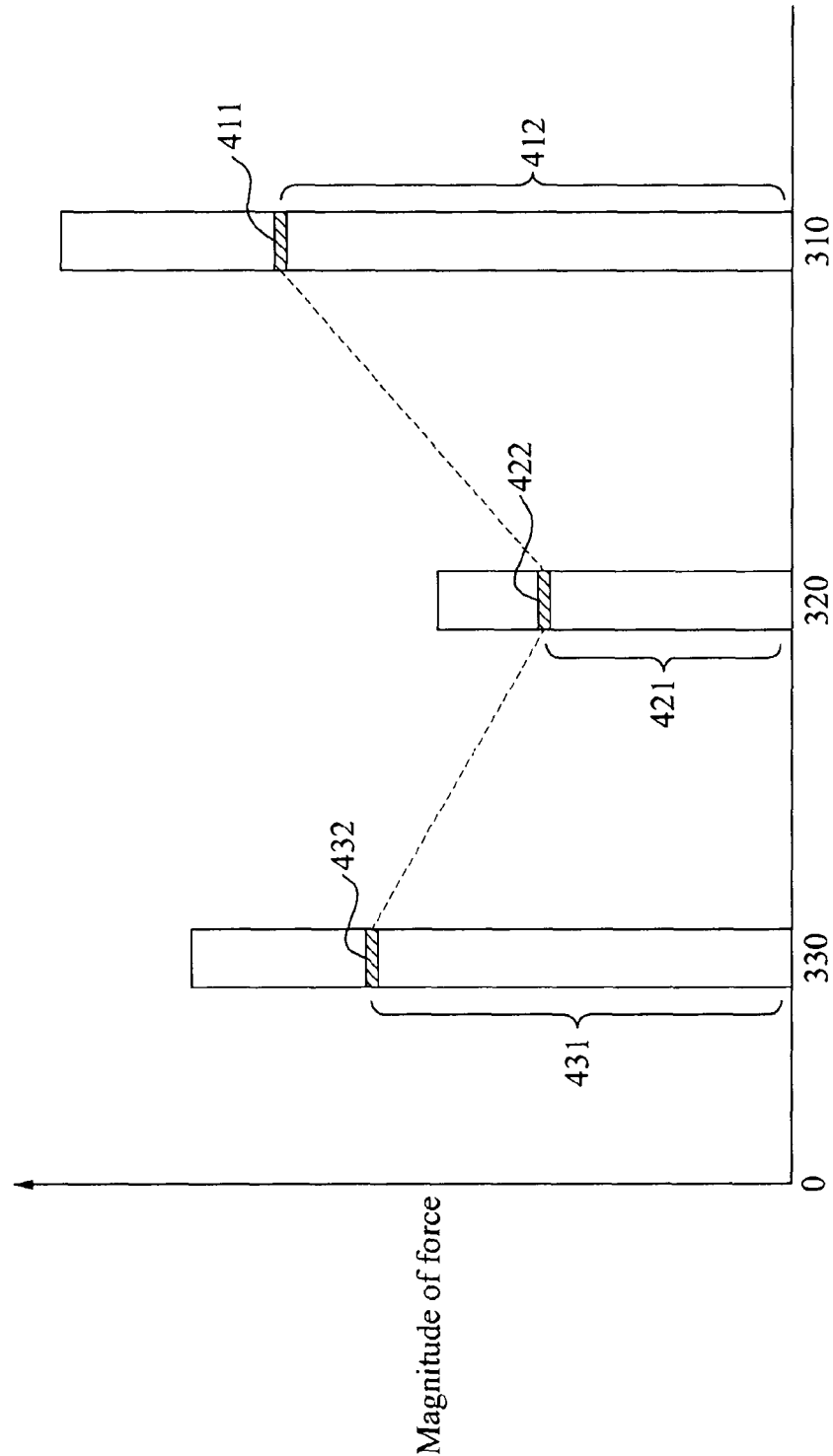

APPARATUS AND METHOD FOR CONTROLLING FORCE TO BE USED FOR MOTION OF SURGICAL ROBOT

CROSS-REFERENCE TO RELATED APPLICATIONS

This application claims the priority benefit of Korean Patent Application No. 10-2012-0045523, filed on Apr. 30, 2012, in the Korean Intellectual Property Office, the disclosure of which is incorporated herein by reference.

BACKGROUND

1. Field

The following description relates to an apparatus and method for controlling a force to be used for a motion of a surgical robot based on a user input, and more particularly, to an apparatus and method for scaling a motion of the surgical robot based on a type of object gripped by the surgical robot.

2. Description of the Related Art

Haptic feedback technology for generating and transferring an artificial sensation is being developed in order to enable a user to feel a sensation of gripping an object in reality when the user controls an object intuitively in a virtual space, or controls a robot remotely.

A surgical robot may use haptic feedback technology for providing a user with a sensation of touching an object or an organ of a patient, for example a soft tissue, directly, by adjusting a level of a load to be provided to a user by an apparatus for controlling the surgical robot remotely when the surgical robot touches a surgical instrument or the organ of the patient.

However, because the surgical robot may be operated remotely, a time lag may occur between a time when the user touches the object or the organ directly and a time when the user receives a feedback regarding a magnitude of a force exerted by the user although the haptic feedback technology is used.

For example, in a case in which the user performs a surgery directly, the user may relax a grip immediately when the user feels a suture being pulled overly hard such that a breakage of the suture may be prevented. However, in a case in which the user performs the surgery using the surgical robot, the user may feel the suture being pulled overly hard through a feedback after the suture has already broken due to a relatively strong force.

In addition, there may be various types of sutures, and the sutures may be broken at different magnitudes of force depending on the types of sutures. When the user performs the surgery directly, the user may sense a state of a suture with minute fingertip contact. However, when the user uses the surgical robot, feedback of a sensation related to the suture may be difficult.

Accordingly, there is a demand for a method of preventing damage to a surgical instrument or an organ and increasing stability of a surgical robot during a surgery, by controlling a level of a feedback or a motion of the surgical robot based on a type of soft tissue, and a type of instrument, such as a suture, for example.

SUMMARY

The foregoing and/or other aspects are achieved by providing an apparatus and method for controlling a force to be used for a motion of a surgical robot based on a user input, and more particularly, to an apparatus and method for scaling a motion of the surgical robot based on a type of object gripped by the surgical robot.

The following description relates to a method of controlling a surgical robot such that the force applied by the robot is related to a force applied by a user controlling the robot, but is adapted to adjust the force applied by the robot depending on the type of implement used by the robot and the material on which the robot is using the implement. The method may provide feedback to the user providing information regarding the adjusted force.

Example embodiments may include an apparatus and method that may control a motion of a surgical robot by scaling a magnitude of a force input by a user to a threshold value, thereby preventing damage to an object, when the magnitude of the input force is greater than the threshold value at which the object is likely to be damaged.

Example embodiments may include an apparatus and method that may provide a user with information about a proximity of a magnitude of a force input by the user to a threshold value of an object, by generating feedback information based on a ratio of a magnitude of a force exerted on the object by a surgical robot to the threshold value at which the object is undamaged.

Example embodiments may include an apparatus and method that may scale a magnitude of a force input by a user, based on a type of object, whereby a surgical robot may automatically perform a motion on objects using an optimized force although the user does not control the magnitude of the force minutely based on the type of object gripped by the surgical robot.

Additional aspects of embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of embodiments, taken in conjunction with the accompanying drawings of which:

FIGS. 2A through 2D illustrate a configuration of a robot control apparatus according to example embodiments;

FIG. 3 illustrates an example of a process of preventing damage to an object according to example embodiments;

FIG. 4 illustrates an example of a process of scaling a magnitude of a force input by a user according to example embodiments;

DETAILED DESCRIPTION

Figure 1:
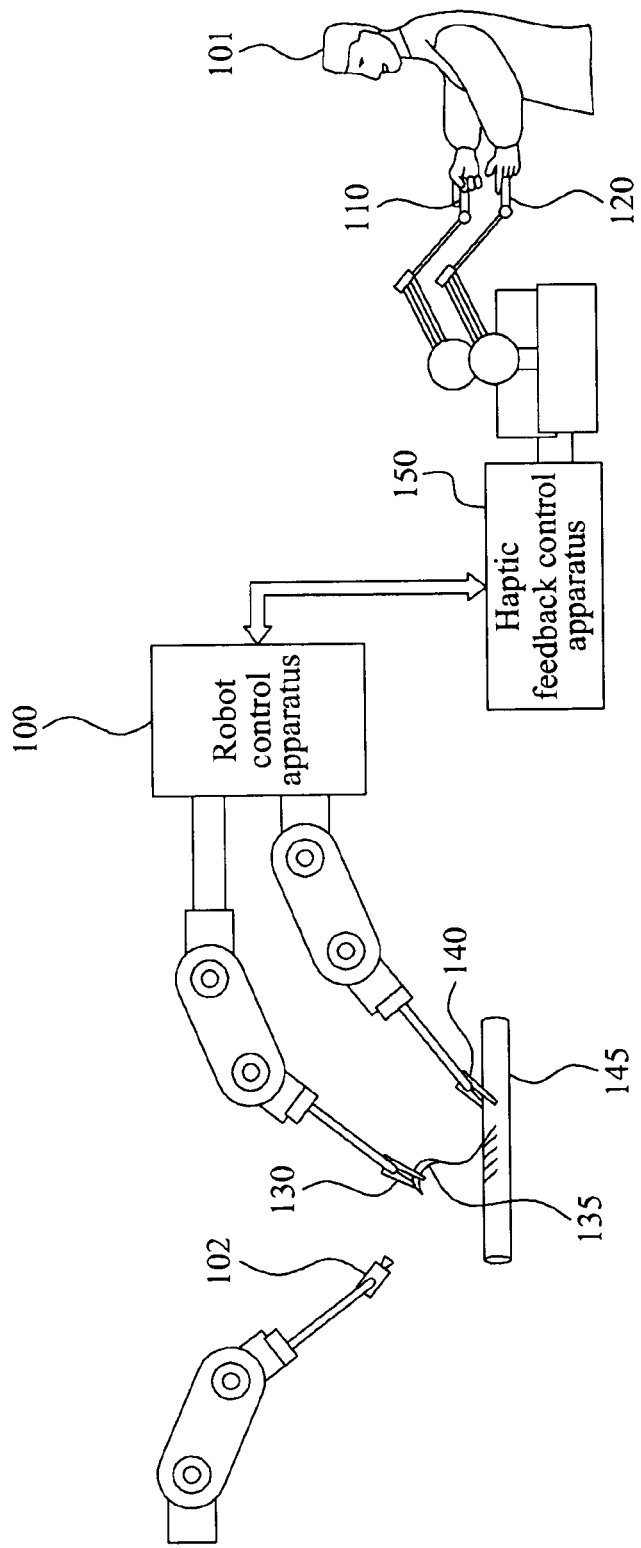
FIG. 1 illustrates a surgical robot system according to example embodiments.

Reference will now be made in detail to embodiments, examples of which are illustrated in the accompanying drawings, wherein like reference numerals refer to like elements throughout. Embodiments are described below to explain the present disclosure by referring to the figures.

FIG. 1 illustrates a surgical robot system according to example embodiments.

Referring to FIG. 1, when a user 101 manipulates a controller 110 and a controller 120 with both hands while viewing images being captured by a camera 102, a robot control apparatus 100 may control a motion of a surgical robot 130 and a motion of a surgical robot 140 based on a motion of the controller 110 and a motion of the controller 120, respectively, and the surgical robot 130 and the surgical robot 140 may move while gripping a tissue 145 of a patient, such as an organ or a soft tissue, for example, or a needle 135 with a suture. In this instance, the surgical robot 130 may be operated based on a control of the controller 110, and the surgical robot 140 may be operated based on a control of the controller 120.

In this instance, the robot control apparatus 100 may measure a motion direction in which the surgical robot 130 or 140 grips the needle 135 or the tissue 145, or a magnitude of a force at which the surgical robot 130 or 140 grips the needle 135 or the tissue 145, using sensors attached to the surgical robot 130 and the surgical robot 140. The robot control apparatus may generate feedback information based on the measured motion direction or the measured magnitude of the force, and may transmit the generated feedback information to a haptic feedback control apparatus 150.

The haptic feedback control apparatus 150 may provide the user 101 with a sensation of touching the needle 135 or the tissue 145 in reality, by controlling the controller 110 or 120 based on the feedback information received from the robot control apparatus 100. For example, the haptic feedback control apparatus 150 may change an elasticity of a portion of the controller 110 or 120 that is gripped with a hand, based on a strength at which the surgical robot 130 or 140 grips the needle 135 or the tissue 145, thereby enabling the user 101 to feel the strength at which the surgical robot 130 or 140 grips the needle 135 or the tissue 145.

The haptic feedback control apparatus 150 may move the portion of the controller 110 or 120 gripped with the hand, based on the feedback information received from the robot control apparatus 100, thereby enabling the user 101 to feel the motion direction of the surgical robot 130 or 140.

In this instance, a suture may have various thicknesses and properties depending on usage. Accordingly, sutures may have different durabilities against forces applied during a process of tying the sutures, or a process of stitching a tissue with the sutures. That is, when the surgical robot 130 or 140 identically applies a force suitable for a suture A to a suture B having a durability lower than a durability of the suture A, the suture B may be likely to break during the process. In addition, the tissue 145, which may be a blood vessel or an internal organ, for example, may be damaged at different magnitudes of force, depending on thicknesses and properties of the tissue 145.

Accordingly, the robot control apparatus 100 may prevent such damage to an instrument or a tissue by scaling feedback information or the motion of the surgical robot 130 or 140 based on a type of object, such as the tissue, or the instrument, for example, gripped by the surgical robot 130 or 140. In this instance, the robot control apparatus 100 may receive an input of the type of object from the user 101, or may determine the type of object based on a force at which the surgical robot 130 or 140 grips the object.

For example, it may be assumed that a magnitude of a force to be used for the motion of the surgical robot 130 that may be input by the user 101 through the controller 110 may be in the range of approximately 0 to approximately 100, and a durability of the suture used to thread the needle 135 gripped by the surgical robot 130 may be in the range of approximately 0 to approximately 50. In this instance, when the user 101 applies a force of approximately 70 to the controller 110, the robot control apparatus 100 may control the surgical robot 130 by scaling the magnitude of the force input by the user 101 from the force of approximately 70 to a force of approximately 35, thereby preventing breakage of the suture. Also, the robot control apparatus 100 may transfer feedback information about a motion of the surgical robot 130 by scaling the feedback information to a force of approximately 100, thereby reporting, to the user 101, that a magnitude of a force at which the suture is in danger of being broken is input.

In addition, the robot control apparatus 100 may transmit the feedback information about the motion of the surgical robot 130 that operates using the force of approximately 35, by scaling the feedback information to the force of approximately 70, thereby providing the user 101 with a sensation of controlling the surgical robot 130 with the force of approximately 70.

That is, the robot control apparatus 100 may automatically scale a magnitude of a force exerted by the surgical robot 130 or 140 based on a type of object gripped by the surgical robot 130 or 140, thereby preventing damage to the instrument or the tissue although the user 101 applies a relatively strong force by mistake.

In addition, the robot control apparatus 100 may scale feedback information about the motion of the surgical robot 130 or 140, based on the type of the object gripped by the surgical robot 130 or 140, thereby reporting, to the user 101, that the user 101 applies a force at which the object may be damaged. Further, the robot control apparatus 100 may provide the user 101 with a sensation corresponding to the motion of the surgical robot 130 or 140, based on the force input by the user 101.

Although it is described that the robot control apparatus 100 may control the motion of the surgical robot 130 or 140, and may scale the feedback information, the haptic feedback control apparatus 150 may scale a magnitude of a force or a motion direction before the motion of the controller 110 or 120 is transmitted to the robot control apparatus 100, depending on example embodiments. In this instance, the haptic feedback control apparatus 150 may scale the feedback information received from the robot control apparatus 100. In addition, the haptic feedback control apparatus 150 may receive, from the user 101 or the robot control apparatus 100, information about the type of object gripped by the surgical robot 130 or 140.

Figure 2A:
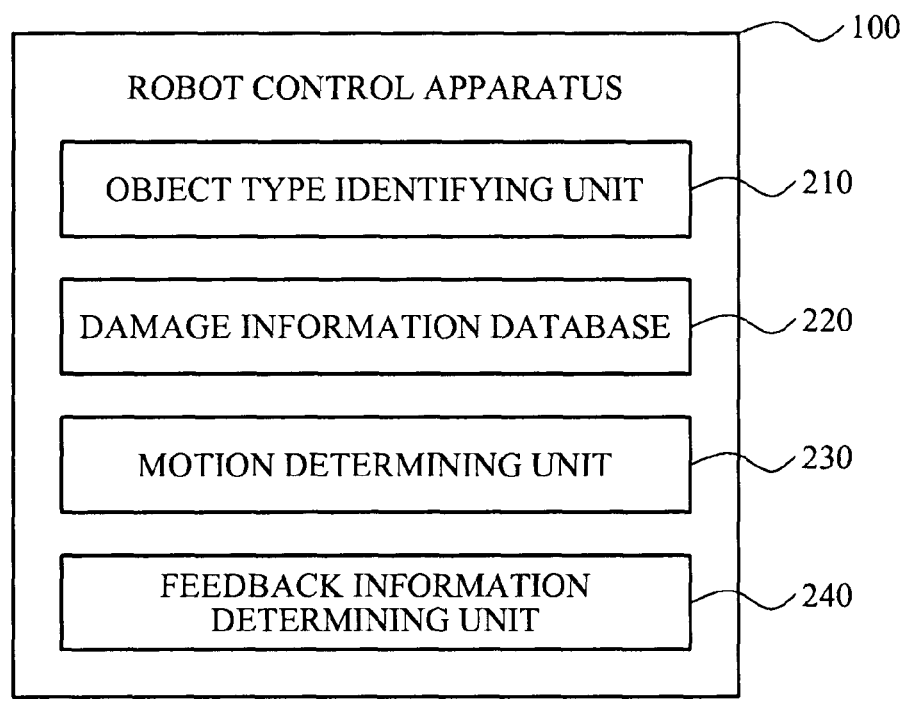

FIG. 2A illustrates a configuration of the robot control apparatus 100 of FIG. 1 according to example embodiments.

Referring to FIG. 2A, the robot control apparatus 100 may include an object type identifying unit 210, a damage information database 220, a motion determining unit 230, and a feedback information determining unit 240.

The object type identifying unit 210 may identify a type of object gripped by a surgical robot.

In particular, the object type identifying unit 210 may determine the type of object based on a grip strength corresponding to a force at which the surgical robot grips the object, or based on object type information input by a user. For example, when there are objects having different thicknesses, such as a blood vessel, a suture, or an intestinal tract, for example, the surgical robot may grip the objects at different magnitudes of force. Accordingly, the object type identifying unit 210 may identify the type of object, based on a thickness of the object or a magnitude of the force at which the surgical robot grips the object. Also, when the user selects an instrument to be used, such as a suture, for example, using a separate input apparatus or a controller, the object type identifying unit 210 may receive information related to the instrument selected by the user, or information related to a type of the instrument.

The damage information database 220 may store and manage damage information for each object.

In this instance, the damage information may include information related to a direction in which the object may be damaged or a force at which the object may be damaged. For example, the damage information may include at least one threshold value associated with damage to an object, as shown in Table 1 illustrated in FIG. 2B.

In this instance, the at least one threshold value associated with the damage to the object may include at least one of a stiffness corresponding to a threshold value at which the object may be deformed temporarily, a fracture force corresponding to a threshold value at which the object may be destroyed, and a yield strength corresponding to a threshold value at which the object may be deformed permanently.

The damage information database 220 may store the at least one threshold value associated with the damage to the object, by classifying a stretch corresponding to a force of pulling the object and a compression corresponding to a force of pressing the object, thereby enabling the at least one threshold value to correspond to a case of the surgical robot pulling or pushing a corresponding object.

The damage information database 220 may classify types of objects into a surgical instrument and a tissue of a patient, such as an organ, for example, and further classify types of surgical instruments or types of tissues. In addition, with respect to an instrument or a tissue having a low durability, such as a suture or a blood vessel, foe example, the damage information database 220 may store damage information for each detailed item, such as a name of the suture or a type of the blood vessel, for example.

The motion determining unit 230 may determine a motion of the surgical robot corresponding to a user input, based on the identified type of object. In particular, the motion determining unit 230 may search the damage information database 220 for damage information corresponding to the type of object identified by the object type identifying unit 210. The motion determining unit 230 may scale a force to be used for the motion of the surgical robot, or may restrict a motion direction of the surgical robot corresponding to the user input, based on found damage information. In this instance, the force to be scaled by the motion determining unit 230 may include at least one of a magnitude of a force at which the surgical robot grips the object, a magnitude of a force at which the surgical robot pulls or pushes the object, and a distance by which the surgical robot pulls or pushes the object.

For example, the motion determining unit 230 may determine whether the motion of the surgical robot corresponding to the user input corresponds to a motion performed by applying a force greater than or equal to a threshold value, based on the damage information. In this instance, when the motion of the surgical robot corresponding to the user input corresponds to a motion performed by applying a force greater than or equal to the threshold value, the motion determining unit 230 may determine the motion of the surgical robot to be performed using a force having a magnitude less than the force input by the user.

In this instance, the motion determining unit 230 may scale a magnitude of the force to be used for the motion of the surgical robot corresponding to the user input, based on a ratio of the magnitude of the force corresponding to the user input to a maximum magnitude of a force available for the surgical robot. In addition, the motion determining unit 230 may scale the magnitude of the force to be used for the motion of the surgical robot corresponding to the user input, based on a threshold value related to a direction corresponding to the user input in the damage information.

For example, when the ratio of the force corresponding to the user input to the maximum magnitude of the force available for the surgical robot corresponds to 7:10, the motion determining unit 230 may determine that the user exerted approximately 70% of a force, and may scale approximately 70% of the threshold value related to the direction corresponding to the user input, in the damage information, to the magnitude of the force to be used for the motion of the surgical robot corresponding to the user input.

In addition, the motion determining unit 230 may set a motion direction of the surgical robot in which the object is likely to be damaged to be a restricted direction, based on a motion direction of the surgical robot and the magnitude of the force to be used for the motion of the surgical robot. In this instance, when the motion direction of the robot corresponding to the user input is performed in the restricted direction, the motion determining unit 230 may restrict the motion of the robot with respect to the restricted direction.

For example, when the surgical robot pulls, based on a user input, a suture with a force having a magnitude greater than a threshold value at which the suture is durable, the motion determining unit 230 may scale the magnitude of the force to be used for the motion of the surgical robot to be lower than the threshold value at which the suture is durable. In this instance, when a user provides an input to control the surgical robot to move in a direction of pulling the suture, the motion determining unit 230 may restrict the motion of the surgical robot moving in the direction of pulling the suture based on the user input, thereby preventing the suture from being broken due to a motion greater than the threshold value.

The feedback information determining unit 240 may determine feedback information based on the motion of the surgical robot and the identified type of object. In this instance, the feedback information determining unit 230 may transmit the determined feedback information to the haptic feedback control apparatus 150, and the haptic feedback control apparatus 150 may provide a feedback to the user, based on the received feedback information.

In this instance, the feedback information determining unit 240 may determine the feedback information based on at least one of a magnitude of the force input by the user and a relationship between the magnitude of the force used by the user and the threshold value.

In particular, when the feedback information is determined based on the magnitude of the force used by the user, the feedback information determining unit 240 may scale the magnitude of the force corresponding to the motion of the surgical robot in the feedback information, based on a ratio of a magnitude of the force used for the motion of the surgical robot corresponding to the user input to a maximum magnitude of a force available for the surgical robot.

For example, when the ratio of the force corresponding to the user input to the maximum magnitude of the force available for the surgical robot corresponds to 7:10, the motion determining unit 230 may determine that the user exerted approximately 70% of a force, and may scale approximately 70% of the threshold value related to the direction corresponding to the user input, in the damage information, to the magnitude of the force to be used for the motion of the surgical robot corresponding to the user input. In this instance, because the feedback information corresponding to approximately 70% of the threshold value may be less than the magnitude of the force input by the user, when the feedback information corresponding to approximately 70% of the threshold value is provided to the user, the user may be likely to determine that the force being used by the user is a relatively weak force. Accordingly, the feedback information determining unit 240 may scale a feedback about the magnitude of the force used for the motion of the surgical robot corresponding to approximately 70% of the threshold value to approximately 70% of the maximum magnitude of the force available for the surgical robot, thereby generating feedback information informing the user that approximately 70% of the entire force is being used.

When the feedback information is determined based on the relationship between the magnitude of the force used by the user and the threshold value, the feedback information determining unit 240 may scale the magnitude of the force corresponding to the motion of the surgical robot in the feedback information, based on a ratio of the magnitude of the force input by the user to a threshold value of the object gripped by the surgical robot.

For example, when the ratio of the magnitude of the force corresponding to the user input to the maximum magnitude of the force available for the surgical robot corresponds to 7:10, and the magnitude of the force corresponding to the user input is close to a threshold value of a corresponding object, feedback information corresponding to the magnitude of the force used for the motion of the surgical robot may be provided to the user. In this instance, the user may determine that approximately 70% of the entire force is being used by the user and thus, the magnitude of the force may be increased further. Accordingly, the feedback information determining unit 240 may scale the feedback about the magnitude of the force used for the motion of the surgical robot to be close to the maximum magnitude of the force available for the surgical robot, based on the relationship between the magnitude of the force used by the user and the threshold value, thereby generating feedback information informing the user that the magnitude of the force used is close to the threshold value.

That is, when the motion determining unit 230 automatically scales the magnitude of the force input by the user based on the damage information of the object, the feedback information determining unit 240 may generate the feedback information based on the magnitude of the force input by the user, thereby enabling the user to feel a proportion of the force used by the user. In addition, when the motion determining unit 230 scales the magnitude of the force input by the user to be less than or equal to the threshold value of the object, the feedback information determining unit 240 may generate the feedback information based on a difference between the magnitude of the force input by the user and the threshold value, thereby inducing the user to control the magnitude of the force to be input by the user, based on the generated feedback information.

When the motion determining unit 230 restricts a motion direction of the surgical robot corresponding to the user input, the feedback information determining unit 240 may incorporate, into the feedback information, control information for precluding the motion of the surgical robot in a direction corresponding to the user input.

For example, when the motion determining unit 230 restricts the motion of the surgical robot in a direction of pulling a suture based on the user input, the feedback information determining unit 240 may incorporate, into the feedback information, control information for precluding the motion of the surgical robot in the direction of pulling the suture. In this instance, when the user desires to move the controller in the direction of pulling the suture, the haptic feedback control apparatus 150 may provide the user with a feedback of a feeling similar to a feeling of the controller touching a wall, or may preclude the controller from moving in such a direction. Accordingly, the user is prevented from controlling the controller in a direction in which the suture is likely to be broken.

FIG. 3 illustrates an example of a process of preventing damage to an object according to example embodiments. Here, the process of FIG. 3 may be performed by the surgical robot system of FIG. 1.

As shown in FIG. 3, a maximum value, in a range 310, of a force received by the haptic feedback control apparatus 150 through the controller 110 or 120, or fed back to a user may be greater than a maximum value, in a range 320, of a force applied without damaging a suture, and a maximum value, in a range 320, of a force applied without damaging a tissue.

In this instance, the maximum value in the range 310 of the force may be identical to a maximum value of a force available for a surgical robot based on control of the robot control apparatus 100. That is, the range 310 of the force input by the user or fed back to the user may be in a range of approximately 0 to the maximum value of the force available for the surgical robot. In addition, the range 320 of the force applied without damaging the suture may have a value in a range from approximately 0 to a threshold value of the suture, and the range 330 of the force applied without damaging the tissue may have a value in a range from approximately 0 to a threshold value of the tissue.

When the user inputs a force 311 of an identical magnitude through the controller 110 and the controller 120 while the surgical robot 130 is gripping the suture and the surgical robot 140 is gripping the tissue, the robot control apparatus 100 may compare the magnitude of the input force 311 to the threshold value of the suture and the threshold value of the tissue.

In this instance, because a magnitude of the force 311 is greater than the threshold value of the suture, as shown in FIG. 3, when the surgical robot 130 performs a motion using a force 321 of which a magnitude is identical to the magnitude of the force 311, the suture may likely be damaged. Accordingly, the robot control apparatus 100 may scale the magnitude of the force 321 to a magnitude of a force 322 based on the threshold value of the suture, and may control the surgical robot 130 to move using the force 322.

Also, because the threshold value of the tissue is greater than the magnitude of the force 311, the robot control apparatus 100 may control the surgical robot 140 to move using a force 331 of which a magnitude is identical to the magnitude of the force 311.

In this instance, because the magnitude of the force 322 used for the motion of the surgical robot 130 corresponds to the maximum value in the range 320 of the force applied without damaging the suture, the robot control apparatus 100 may generate feedback information corresponding to a maximum value in the range 310 of the force, that is, a magnitude of a force 312, to provide the user with a feedback that the user used a force having a magnitude corresponding to the threshold value of the suture. In this instance, the haptic feedback control apparatus 150 may provide the user with a feedback that the motion of the surgical robot 130 is performed at the maximum value of the force, based on the feedback information corresponding to the maximum value in the range 310 of the force, that is, the magnitude of the force 312, through the controller 110.

In addition, a ratio 332 of the magnitude of the force 331 used for the motion of the surgical robot 140 to the threshold value of the tissue may differ from a ratio 313 of the magnitude of the force 311 to the maximum value of the force available for the surgical robot. As illustrated in FIG. 3, because the maximum value in the range 330 of the force is less than the maximum value in the range 310 of the force, when the ratio 313 of the magnitude of the force 311 to the maximum magnitude of the force available for the surgical robot corresponds to approximately 70% of the range 310 of the force, the ratio 332 of the magnitude of the force 331, which is identical to the magnitude of the force 311, to the threshold value of the tissue may correspond to approximately 90% of the range 330 of the force.

Accordingly, the robot control apparatus 100 may generate feedback information corresponding to approximately 90% of the maximum value in the range 310 of the force, that is, a magnitude of a force 314, in order to provide the user with a feedback that the surgical robot 140 applied, to the tissue, a force corresponding to approximately 90% of the threshold value of the tissue although the user used approximately 70% of the force 310. In this instance, the haptic feedback control apparatus 150 may provide the user with a feedback that the motion of the surgical robot 140 is performed using approximately 90% of the force 310, based on the feedback information corresponding to approximately 90% of the maximum value in the range 310 of the force, that is, the magnitude of the force 314, through the controller 110.

That is, when a magnitude of a force input by the user is greater than a threshold value at which an object is likely to be damaged, the robot control apparatus 100 may control a surgical robot by scaling the magnitude of the input force to the threshold value. Accordingly, damage to the object is prevented.

In addition, by generating feedback information based on a ratio of the magnitude of the force applied by the surgical robot to the object to the threshold value at which the object may be undamaged, the robot control apparatus 100 may provide the user with information regarding a proximity of the magnitude of the force input by the user to the threshold value of the object.

FIG. 4 illustrates an example of a process of scaling a magnitude of a force input by a user according to example embodiments. Here, the process of FIG. 4 may be performed by the surgical robot system of FIG. 1.

The robot control apparatus 100 may control a surgical robot by scaling a magnitude of the force input by the user, based on a threshold value of an object.

For example, when the user inputs a force 411 of an identical magnitude through the controller 110 and the controller 120 while the surgical robot 130 and the surgical robot 140 are gripping different types of objects, respectively, the robot control apparatus 100 may control a magnitude of a force 421 to be used for a motion of the surgical robot 130 and a magnitude of a force 431 to be used for a motion of the surgical robot 140, differently, by scaling the magnitude of the input force 411.

In particular, the robot control apparatus 100 may verify a ratio 412 of a magnitude of the force 411 input by the user to a maximum magnitude of a force available for the surgical robot, in a range 310, of a force input to the haptic feedback control apparatus 150 by the user or fed back to the user.

When the ratio 412 of the magnitude of the force 411 input by the user to the maximum magnitude of the force available for the surgical robot corresponds to approximately 70% of the range 310 of the force, the robot control apparatus 100 may identify the magnitude of the force 422 at which a ratio 421 of the magnitude of the force used for the motion of the surgical robot 130 to a threshold value of a suture corresponds to approximately 70%, of a range 320, of a force applied without damaging the suture. The robot control apparatus 100 may determine the identified magnitude of the force 422 to be the magnitude of the force to be used for the motion of the surgical robot 130. In addition, the robot control apparatus 100 may identify the magnitude of the force 432 at which a ratio 431 of the magnitude of the force used for the motion of the surgical robot 140 to a threshold value of a tissue, such as an organ, for example, corresponds to approximately 70%, of a range 330, of a force applied without damaging the tissue. The robot control apparatus 100 may determine the identified magnitude of the force 432 to be the magnitude of the force to be used for the motion of the surgical robot 140.

In addition, the robot control apparatus 100 may generate feedback information informing that each of the motion of the surgical robot 130 and the motion the surgical robot 140 is performed using approximately 70% of a corresponding force. In this instance, the haptic feedback control apparatus 150 may provide the user with a feedback that each of the surgical robots is operated using approximately 70% of the force, based on the feedback information generated by the robot control apparatus 100, through each controller.

That is, although the user inputs a force of an identical magnitude, the robot control apparatus 100 may scale the magnitude of the force based on a type of object, thereby enabling a surgical robot to perform a motion on objects having various durabilities, using an optimized force.

For example, it may be assumed that there may be a first scheme of tying a suture tightly at a maximum magnitude of a force, and a second scheme of tying a suture using a medium magnitude of a force so as not to be untied, and a first suture may have a threshold value two times greater than a threshold value of a second suture. Here, the threshold value may refer to a value at which a corresponding suture may be damaged. In this instance, when a user ties the first suture and the second suture at an identical magnitude of a force, using the second scheme, there may be a difference between a magnitude of the input force and a threshold value. Accordingly, the first suture may be tied by the second scheme. However, the second suture may be tied as if the second suture is tied by the first method because the second suture may be tied using a force corresponding to the threshold value of the second suture.

Accordingly, when the user ties the first suture and the second suture at an identical magnitude of a force by the second scheme, the robot control apparatus 100 may tie the second suture using a force corresponding to approximately 50% of the threshold value of the second suture, thereby tying the second suture by an identical scheme of tying the first suture.

That is, the robot control apparatus 100 may scale a magnitude of a force of an identical magnitude based on a type of object, whereby a surgical robot may automatically perform a motion on objects using an optimized force although the user does not control the force minutely based on the type of object gripped by the surgical robot.

Figure 5:
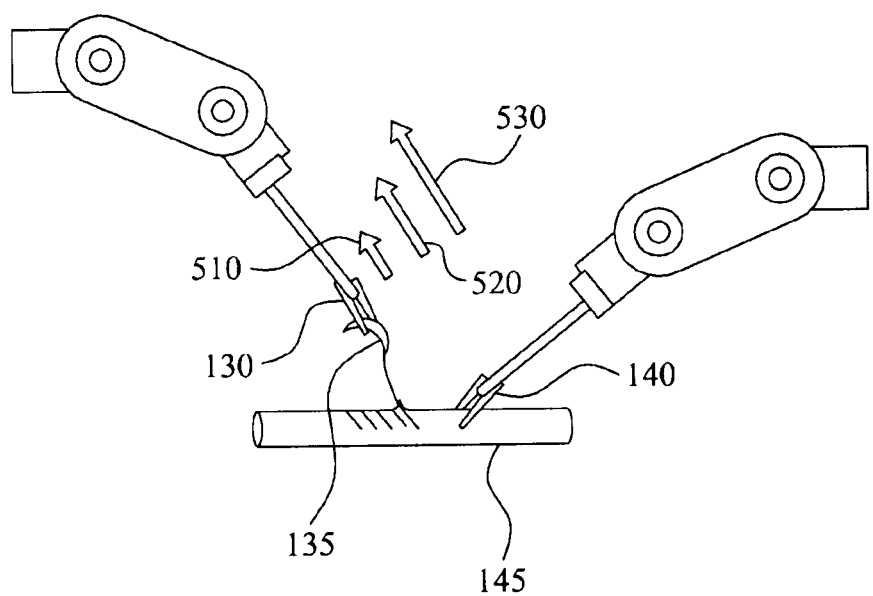
FIG. 5 illustrates an example of a process of determining a magnitude of a force to be used for a motion of a surgical robot based on a type of suture used to thread a needle gripped by the surgical robot according to example embodiments.

FIG. 5 illustrates an example of a process of determining a magnitude of a force to be used for a motion of a surgical robot based on a type of suture used to thread a needle gripped by the surgical robot according to example embodiments. The process of FIG. 5 may be performed by the surgical robot system of FIG. 1.

As shown in FIG. 5, the robot control apparatus 100 may control the motion of the surgical robot 130 based on a user input while the surgical robot 130 is gripping the needle 135 with a suture and the surgical robot 140 is gripping the tissue 145, such as an organ, for example, of a patient. In this instance, the robot control apparatus 100 may measure a magnitude of a force 510 and a motion direction of the surgical robot 130, and may search for damage information corresponding to a type of the suture used to thread the needle 135, from information about sutures in the damage information database 220 of FIG. 2A, as provided in Table 2 in FIG. 2C.

When a threshold value in damage information corresponding to the type of the suture used to thread the needle 135 is less than a maximum magnitude of a force available for the surgical robot 130 or 140, the robot control apparatus 100 may scale up a magnitude of a force to be fed back to the user to a magnitude of a force 520, thereby reporting, to the user, that the user applied a force with a magnitude close to the threshold value of the suture.

In addition, the robot control apparatus 100 may scale a magnitude of a force to be used by the surgical robot 130 to a magnitude of a force 530, based on the threshold value in the damage information corresponding to the type of the suture used to thread the needle 135, thereby preventing the suture from being damaged due to an excessive magnitude of force, that is, the force 510.

For example, the robot control apparatus 100 may scale a magnitude of a force to be fed back to the user, or a magnitude of a force to be used for a motion of a surgical robot, based on a type of suture, thereby automatically performing a motion using a force of which a magnitude is optimized for the suture to be used by the surgical robot although the user does not minutely control a magnitude of a force to be input every time the user selects another type of suture to be used for a surgery.

Figure 6:
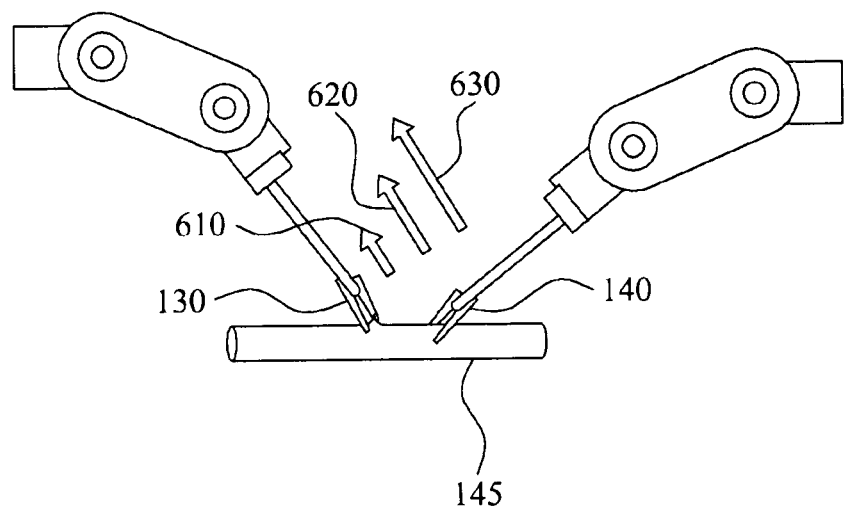
FIG. 6 illustrates an example of a process of determining a magnitude of a force to be used for a motion of a surgical robot based on a type of tissue gripped by the surgical robot according to example embodiments.

FIG. 6 illustrates an example of a process of determining a magnitude of a force to be used for a motion of a surgical robot based on a type of tissue gripped by the surgical robot according to example embodiments. The process of FIG. 6 may be performed by the surgical robot system of FIG. 1.

As shown in FIG. 6, the robot control apparatus 100 may control the motion of the surgical robot 130 based on a user input while the surgical robot 130 and the surgical robot 140 are gripping the tissue 145, such as an organ, for example, of a patient. In this instance, the robot control apparatus 100 may measure a magnitude of a force 610 and a motion direction of the surgical robot 130, and may search for damage information corresponding to a type of the tissue 145, from information about tissues in the damage information database 220 of FIG. 2A, as provided in Table 3 of FIG. 2D.

When a threshold value in damage information corresponding to the type of the tissue 145 is less than a maximum magnitude of a force available for the surgical robot 130 or 140, the robot control apparatus 100 may scale up a magnitude of a force to be fed back to the user to a magnitude of a force 620, thereby reporting, to the user, that the user applied a force with a magnitude close to the threshold value of the tissue.

In addition, the robot control apparatus 100 may scale a magnitude of a force to be used by the surgical robot 130 to a magnitude of a force 630, based on the threshold value in the damage information corresponding to the type of the tissue 145, thereby preventing the tissue 145 from being damaged due to an excessive magnitude of force, that is, the force 610.

That is, the robot control apparatus 100 may scale a magnitude of a force to be fed back to the user, or a magnitude of a force to be used for a motion of a surgical robot, based on a type of tissue gripped by the surgical robot, thereby automatically performing a motion using a force of which a magnitude is optimized for the tissue gripped by the surgical robot although the user does not minutely control a magnitude of a force to be input every time the user grips another type of tissue using the surgical robot during a surgery.

Figure 7:
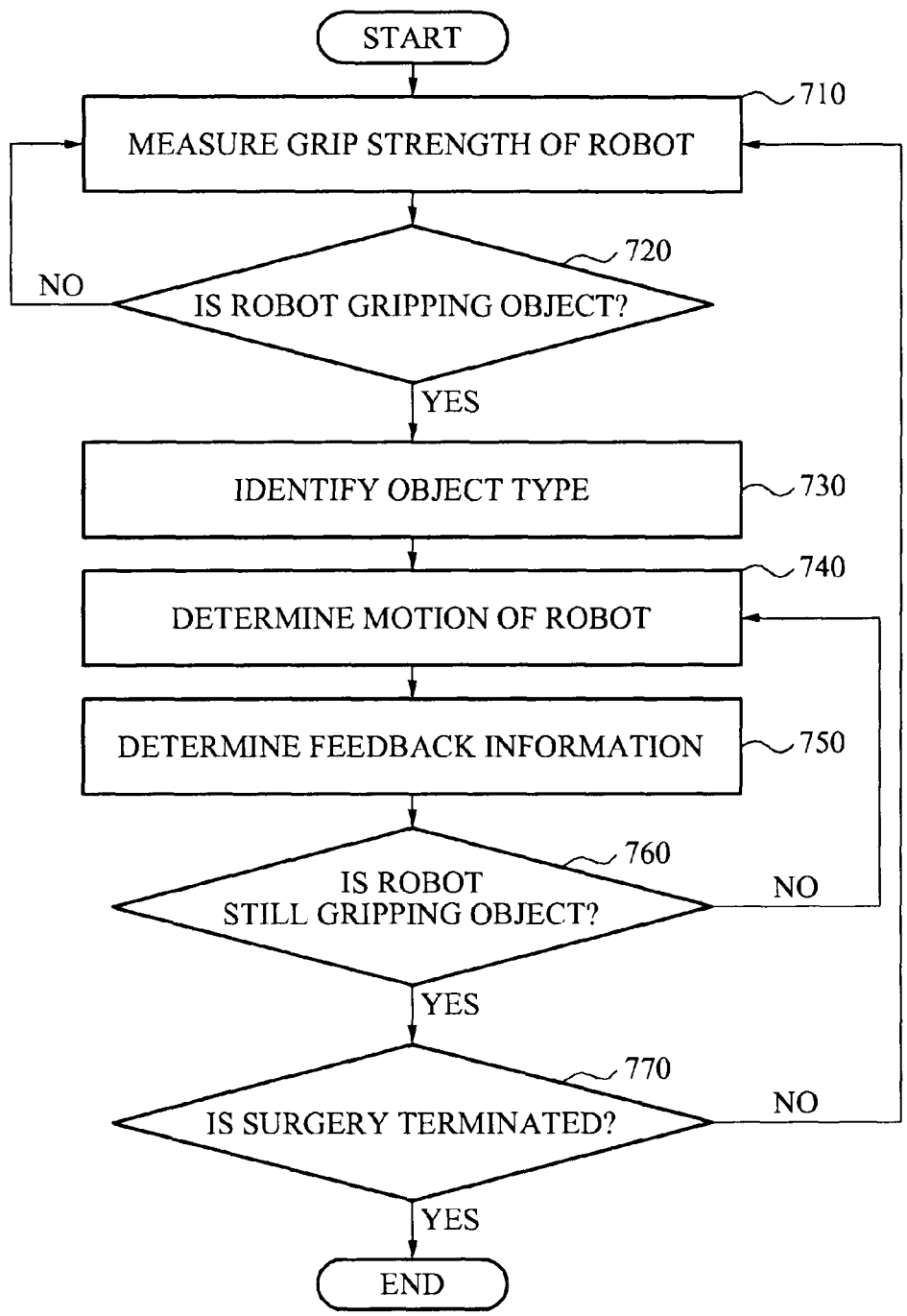
FIG. 7 illustrates a method of controlling a robot according to example embodiments.

FIG. 7 illustrates a method of controlling a robot according to example embodiments. The method of FIG. 7 may be performed by the robot control apparatus 100 of FIG. 2A.

In operation 710, the object type identifying unit 210 may measure a grip strength corresponding to a force at which a surgical robot grips an object, using a sensor installed in the surgical robot.

In operation 720, the object type identifying unit 210 may verify whether the surgical robot is gripping an object, based on the grip strength measured in operation 710. In this instance, when the surgical robot is not gripping an object, the object type identifying unit 210 may repeat the operation 710 until the surgical robot grips an object.

In operation 730, when it is verified that the surgical robot is gripping an object in operation 720, the object type identifying unit 210 may identify a type of object gripped by the surgical robot. In this instance, the object type identifying unit 210 may determine the type of object, based on the grip strength measured in operation 710, or information related to the type of object that is received by a user.

In operation 740, the motion determining unit 230 may determine a motion of the surgical robot corresponding to a user input, based on the type of object identified in operation 730. In particular, the motion determining unit 230 may search the damage information database 230 for damage information corresponding to the identified type of object, and may restrict a motion direction of the surgical robot corresponding to the user input or may scale a magnitude of a force to be used for the motion of the surgical robot, based on found damage information.

In operation 750, the feedback information determining unit 240 may determine feedback information, based on the type of object identified in operation 730 and the motion of the surgical robot determined in operation 740. In this instance, the feedback information determining unit 240 may transmit the determined feedback information to the haptic feedback control apparatus 150 of FIG. 1, and the haptic feedback control apparatus 150 may provide a feedback to the user, based on the received feedback information.

For example, when the motion determining unit 230 restricts a motion of the surgical robot in a direction of pulling a suture based on the user input, the feedback information determining unit 240 may incorporate, into the feedback information, control information for precluding the motion of the surgical robot in the direction of pulling the suture. In this instance, when the user desires to move a controller in the direction of pulling the suture, the haptic feedback control apparatus 150 may provide the user with a feedback of a feeling as if the controller touches a wall, or may preclude the controller from moving in the direction of pulling the suture, thereby preventing the user from controlling the controller in a direction in which the suture is likely to break.

In operation 760, the object type identifying unit 210 may verify whether the surgical robot is still gripping the object identified in operation 720. In this instance, when it is determined that the surgical robot is still gripping the object, the motion determining unit 230 may repeat the operation 740 until the surgical robot releases the object.

When it is verified that the object is released by the surgical robot in operation 760, the object type identifying unit 210 may verify whether a surgery is terminated, in operation 770. In this instance when it is verified that the surgery is yet to be terminated, the object type identifying unit 210 may return to the operation 710, and may maintain a standby state until the surgical robot grips another object.

Figure 8:
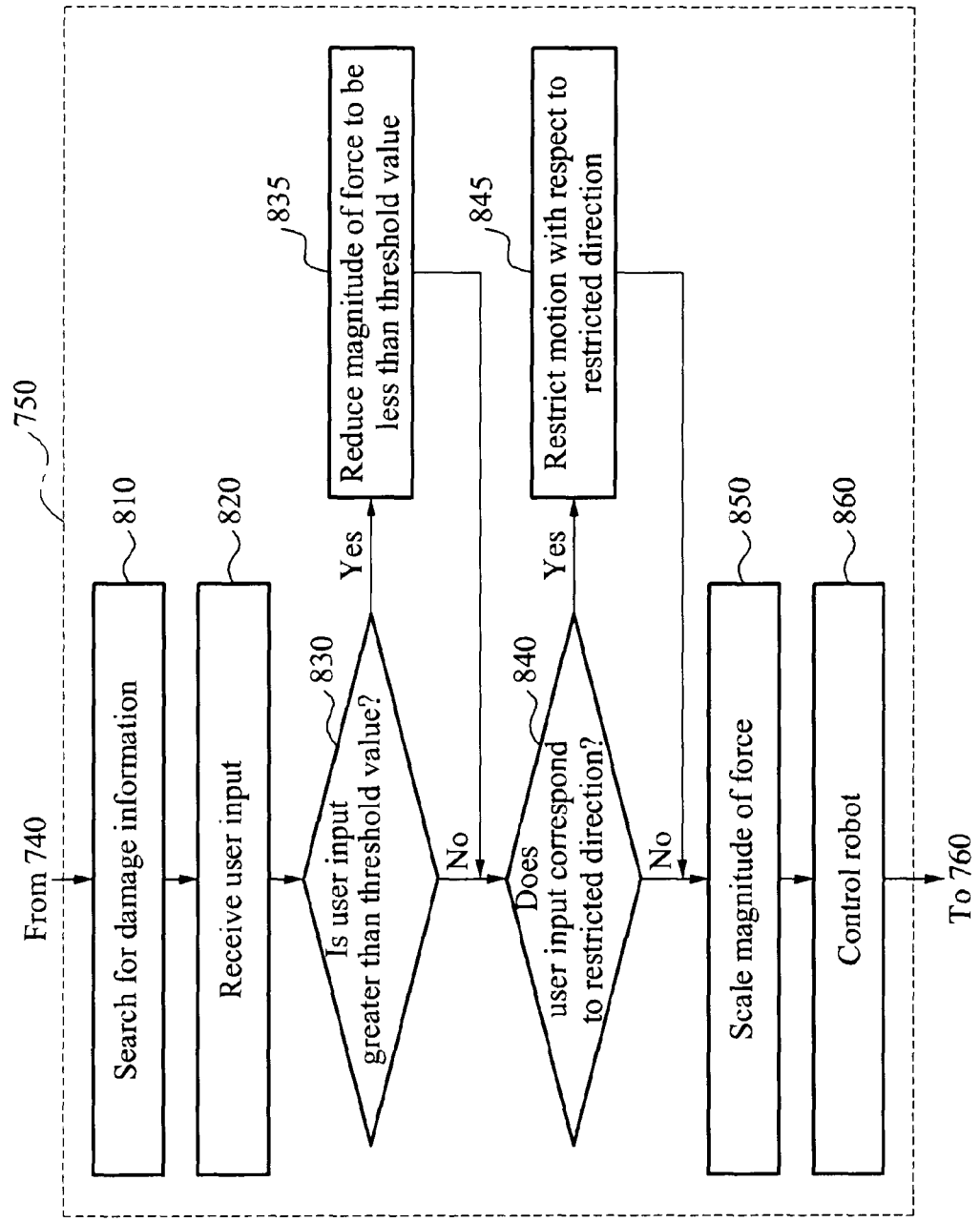
FIG. 8 illustrates a method of determining a motion of a robot according to example embodiments.

FIG. 8 illustrates a method of determining a motion of a robot according to example embodiments. In this instance, operations 810 and 860 may be included in the operation 740 of FIG. 7.

In operation 810, the motion determining unit 230 may search the damage information database 220 for damage information corresponding to the type of object that is identified in operation 730.

In operation 820, the motion determining unit 230 may receive a user input from the haptic feedback control apparatus 150 of FIG. 1. In this instance, the user input may include information related to a motion of the controller 110 or 120 of FIG. 1 controlled by the user.

In operation 830, the motion determining unit 230 may determine whether a motion of the surgical robot corresponding to the user input received in operation 820 corresponds to a motion performed by applying a force greater than or equal to a threshold value, based on damage information found in operation 810. In this instance, when the motion of the surgical robot corresponding to the user input corresponds to a motion performed by applying a force greater than or equal to the threshold value, the motion determining unit 230 may reduce a magnitude of the force used for the motion of the surgical robot corresponding to the user input to be less than the threshold value, in operation 835.

In operation 840, the motion determining unit 230 may determine whether the motion of the surgical robot corresponding to the user input received in operation 820 is performed in a restricted direction, based on the damage information found in operation 810. In this instance, when the motion of the surgical robot corresponding to the user input is performed in the restricted direction, the motion determining unit 230 may restrict the motion of the surgical robot corresponding to the user input with respect to the restricted direction, in operation 845.

In operation 850, the motion determining unit 230 may scale the magnitude of the force used for the motion of the surgical robot corresponding to the user input received in operation 820, based on the damage information found in operation 810. In particular, the motion determining unit 230 may determine a percentage of the force input by the user to be used, and may scale the magnitude of the force, thereby enabling the surgical robot to move using a force corresponding to a result of the determination, based on a threshold value of the object.

In addition, the operation 850 may not be performed according to example embodiments, or may be performed when a user input is received, at a request of the user, after the operations 810 through 845, and operation 860 are performed.

In operation 860, the motion determining unit 230 may determine the motion of the surgical robot, based on the user input received in operation 820, or based on the magnitude of the force scaled in operation 850 and either the magnitude of the force corrected in operation 835 or the direction corrected in operation 845, and may control the surgical robot based on the determined motion.

According to example embodiments, it is possible to prevent damage to an object by controlling a motion of a surgical robot through scaling a magnitude of a force input by a user to a threshold value when the magnitude of the input force is greater than the threshold value at which the object is likely to be damaged.

According to example embodiments, it is possible to provide a user with information about a proximity of a magnitude of a force input by the user to a threshold value of an object, by generating feedback information based on a ratio of a magnitude of a force exerted on the object by a surgical robot to the threshold value at which the object is undamaged.

According to example embodiments, by scaling a magnitude of a force input by a user, based on a type of object, a surgical robot may automatically perform a motion on objects using an optimized force although the user does not control the magnitude of the force minutely based on the type of object gripped by the surgical robot.

The methods according to the above-described embodiments may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of embodiments, or they may be of the kind well-known and available to those having skill in the computer software arts. Examples of computer-readable media include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. The computer-readable media may also be a distributed network, so that the program instructions are stored and executed in a distributed fashion. The program instructions may be executed by one or more processors. The computer-readable media may also be embodied in at least one application specific integrated circuit (ASIC) or Field Programmable Gate Array (FPGA), which executes (processes like a processor) program instructions. Examples of program instructions include both machine code, such as produced by a compiler, and files containing higher level code that may be executed by the computer using an interpreter. The above-described devices may be configured to act as one or more software modules in order to perform the operations of the above-described embodiments, or vice versa.

Although embodiments have been shown and described, it would be appreciated by those skilled in the art that changes may be made in these embodiments without departing from the principles and spirit of the disclosure, the scope of which is defined by the claims and their equivalents.

What is claimed is:

1. An apparatus for controlling a robot, the apparatus comprising:
   an object type identifying unit to identify a type of object that is gripped by the robot; and
   a motion determining unit to determine a motion of the robot corresponding to a user input, based on the identified type of object,
   wherein the motion determining unit scales a magnitude of a force to be used for the motion of the robot corresponding to the user input, based on damage information for each type of object, and
   wherein the damage information comprises information related to a direction or a force in which the object is damaged.

2. The apparatus of claim 1, wherein the damage information comprises a threshold value related to a magnitude of a force at which the object is damaged, for each direction in which the force is applied to the object.

3. The apparatus of claim 1, wherein the motion determining unit scales a magnitude of the force to be used for the motion of the robot corresponding to the user input, based on a ratio of the magnitude of the force corresponding to the user input to a maximum magnitude of a force available for the robot, and a threshold value related to a direction corresponding to the user input in the damage information.

4. The apparatus of claim 1, wherein the motion determining unit sets a motion direction of the robot in which the object is likely to be damaged to be a restricted direction, based on a motion direction of the robot and the magnitude of the force to be used for the motion of the robot, and restricts the motion of the robot corresponding to the user input when the motion of the robot corresponding to the user input is performed in the restricted direction.

5. The apparatus of claim 1, further comprising:
a feedback information determining unit to determine feedback information to be transmitted to a feedback apparatus that provides a feedback to a user based on the identified type of object.

6. The apparatus of claim 5, wherein the feedback information determining unit scales a magnitude of a force corresponding to the motion of the robot in the feedback information, based on a ratio of a magnitude of a force used for the motion of the robot corresponding to the user input to a maximum magnitude of a force available for the robot.

7. The apparatus of claim 5, wherein the feedback information determining unit scales a magnitude of a force corresponding to the motion of the robot in the feedback information, based on a ratio of a magnitude of a force used for the motion of the robot corresponding to the user input to a threshold value related to a direction corresponding to the user input.

8. The apparatus of claim 5, wherein the feedback information determining unit incorporates, into the feedback information, control information for precluding a motion of the robot in a direction corresponding to the user input when the motion determining unit restricts a motion direction of the robot corresponding to the user input.

9. The apparatus of claim 1, wherein the object comprises at least one of a surgical instrument and a tissue of a patient.

10. The apparatus of claim 1, wherein the object type identifying unit identifies the type of object gripped by the robot, based on object type information input by a user.

11. The apparatus of claim 1, wherein the object type identifying unit measures a grip strength corresponding to a force at which the robot grips the object, and identifies the type of object gripped by the robot based on the measured grip strength.

12. A method of controlling a robot, the method comprising:
identifying a type of object that is gripped by the robot; and
determining a motion of the robot corresponding to a user input, based on the identified type of object,
wherein the determining comprises scaling a magnitude of a force to be used for the motion of the robot corresponding to the user input, based on damage information for each type of object, and
wherein the damage information comprises information related to a direction or a force in which the object is damaged.

13. The method of claim 12, wherein the damage information comprises a threshold value related to a magnitude of a force at which the object is damaged, for each direction in which the force is applied to the object.

14. The method of claim 12, wherein the determining comprises scaling a magnitude of the force to be used for the motion of the robot corresponding to the user input, based on a ratio of a magnitude of the force corresponding to the user input to a maximum magnitude of a force available for the robot, and a threshold value related to a direction corresponding to the user input in the damage information.

15. The method of claim 12, wherein the determining comprises setting a motion direction of the robot in which the object is likely to be damaged to be a restricted direction, based on a motion direction of the robot and the magnitude of the force to be used for the motion of the robot, and restricting the motion of the robot corresponding to the user input when the motion of the robot corresponding to the user input is performed in the restricted direction.

16. The method of claim 12, further comprising:
determining feedback information to be transmitted to a feedback apparatus that provides a feedback to a user based on the identified type of object.

17. The method of claim 16, wherein the determining of the feedback information comprises scaling a magnitude of a force corresponding to the motion of the robot in the feedback information, based on a ratio of a magnitude of a force used for the motion of the robot corresponding to the user input to a maximum magnitude of a force available for the robot.

18. The method of claim 16, wherein the determining of the feedback information comprises scaling a magnitude of a force corresponding to the motion of the robot in the feedback information, based on a ratio of a magnitude of a force used for the motion of the robot corresponding to the user input to a threshold value related to a direction corresponding to the user input.

19. The method of claim 16, wherein the determining of the feedback information comprises incorporating, into the feedback information, control information for precluding a motion of the robot in a direction corresponding to the user input when the motion determining unit restricts a motion direction of the robot corresponding to the user input.

20. The method of claim 12, wherein the object comprises at least one of a surgical instrument and a tissue of a patient.

21. The method of claim 12, wherein the identifying comprises identifying the type of object gripped by the robot, based on object type information input by a user.

22. The method of claim 12, wherein the identifying comprises measuring a grip strength corresponding to a force at which the robot grips the object, and identifying the type of object gripped by the robot based on the measured grip strength.

23. A method for controlling a robot, the method comprising:
identifying an implement used by the robot and a material on which the implement is used during the control of the robot;
sensing a magnitude and direction of a force applied by the implement to the material;
scaling a user input based on a predetermined threshold value of the implement, a predetermined threshold value of the material, the applied force, and based on damage information of the material associated with the applied force; and
controlling a motion of the robot based on the scaled user input,
wherein the predetermined threshold values are based on respective physical properties of the identified implement and the identified material, and
wherein the damage information comprises information related to a direction or a force in which the object is damaged.

24. The method of claim 23, further comprising:
providing feedback to the user relating to the controlled motion.

25. The apparatus of claim 1, wherein damage information for different types of objects are stored in a damage information database.

26. The apparatus of claim 2, wherein the threshold value comprises a stiffness corresponding to the threshold value at which the object is deformed temporarily, a fracture force corresponding to the threshold value at which the object is destroyed, and a yield strength corresponding to the threshold value at which the object is deformed permanently.

* * * * *